United States Patent [19]

Bertele et al.

[11] Patent Number: 5,231,882

[45] Date of Patent: Aug. 3, 1993

[54] TESTING DEVICE FOR PERFORMING FOUR-POINT FATIGUE STRENGTH TESTS UNDER ALTERNATING BENDING STRESSES

[75] Inventors: Ludwig Bertele, Weissenhorn; André Papack, Blaustein; Karl-Heinz Wichmann, Achstetten, all of Fed. Rep. of Germany

[73] Assignee: Telefunken Systemtechnik GmbH, Ulm, Fed. Rep. of Germany

[21] Appl. No.: 835,851

[22] Filed: Feb. 18, 1992

[30] Foreign Application Priority Data

Feb. 16, 1991 [DE] Fed. Rep. of Germany ....... 4104822

[51] Int. Cl.$^5$ ............................................. G01N 3/20
[52] U.S. Cl. ........................................................ 73/852
[58] Field of Search ........................ 73/812, 849–854

[56] References Cited

U.S. PATENT DOCUMENTS

| | | |
|---|---|---|
| 4,129,033 | 12/1978 | Otterbach . |
| 4,677,856 | 7/1987 | Fischer .................. 73/850 |
| 4,708,020 | 11/1987 | Lau et al. . |
| 4,730,498 | 3/1988 | Blanch . |
| 4,941,359 | 7/1990 | Quinn et al. . |
| 4,986,132 | 1/1991 | Calomino .............. 73/852 |
| 4,991,446 | 2/1991 | Bechtel ................. 73/852 |

FOREIGN PATENT DOCUMENTS

| | | |
|---|---|---|
| 353509 | 11/1979 | Austria . |
| 120549 | 6/1976 | Fed. Rep. of Germany . |
| 3101422 | 8/1982 | Fed. Rep. of Germany . |
| 3133646 | 3/1983 | Fed. Rep. of Germany . |
| 3711518 | 10/1987 | Fed. Rep. of Germany . |
| 3629131 | 3/1988 | Fed. Rep. of Germany . |
| 277524 | 4/1990 | Fed. Rep. of Germany . |
| 60-107544 | 6/1985 | Japan . |
| 101435 | 9/1923 | Switzerland ............ 73/853 |
| 1051408 | 10/1983 | U.S.S.R. ................. 73/854 |

OTHER PUBLICATIONS

Roell & Korthaus, Amsler-Prüfmaschinen AG (Schaffhausen, Switzerland) *Prüfsysteme*, [Testing Systems], Spec. 205, pp.8–9.
Kiessling, K. G., *Untersuchungen zur Zuverlässigkeit von Lotverbindungen in der SMD-Technik*, [Tests Regarding the Reliability of Solder Connections in SMD Tech., 423–431.

*Primary Examiner*—Robert Raevis
*Attorney, Agent, or Firm*—Spencer, Frank & Schneider

[57] ABSTRACT

A testing device is provided for performing four-point fatigue strength tests of a sample by applying alternating bending stresses to the sample. The device includes four rotary joints. Each rotary joint includes a pair of individual, spaced-apart rollers so that a sample can be guided between the individual rollers of the respective pairs of rollers. Each roller is rotatable about its own longitudinal axis. First and second plates are adapted to be fixed in a force introducing machine so that they are relatively movable toward and away from one another. Four holders are provided, each for supporting a respective one of the rotary joints. Two of the holders are mounted to the first plate, with the third and fourth holders being disposed between the two holders and being mounted to the second plate. Each holder mounts its rotary joint so that the individual rollers of the rotary joint are rotatable about a common rotation axis.

15 Claims, 1 Drawing Sheet

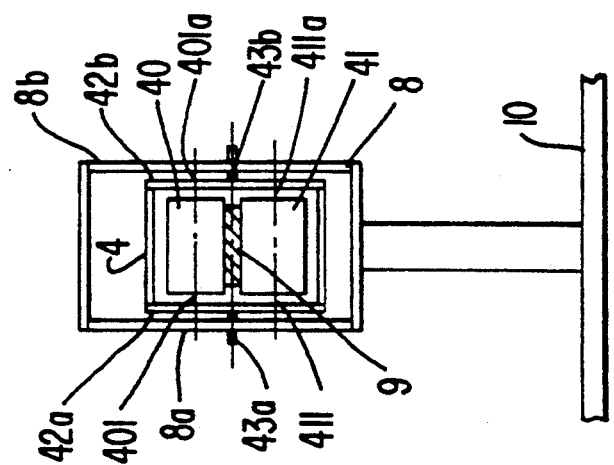
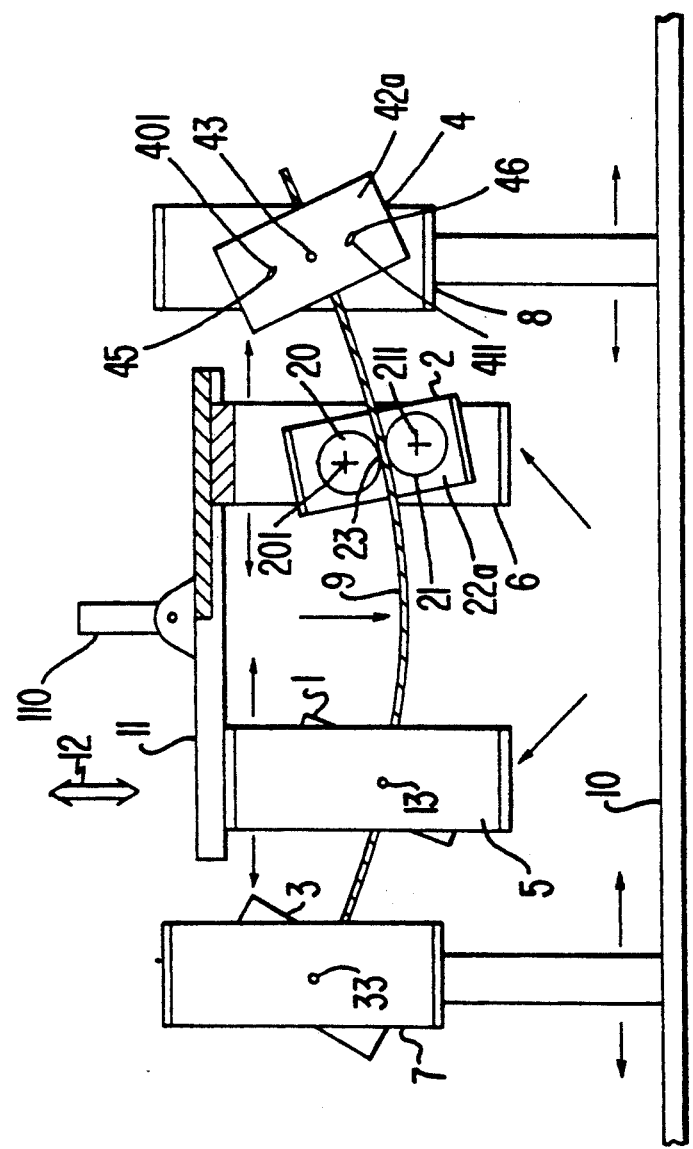

TESTING DEVICE FOR PERFORMING FOUR-POINT FATIGUE STRENGTH TESTS UNDER ALTERNATING BENDING STRESSES

CROSS REFERENCE TO RELATED APPLICATIONS

The present application claims the rights of priority with respect to application Ser. No. P 41 04 822.9 filed Feb. 16, 1991 in Germany, the subject matter of which is incorporated herein by reference.

BACKGROUND OF THE INVENTION

The present invention relates to a testing device for performing four-point fatigue strength tests of a sample, such as a printed circuit board, by applying alternating bending stresses to the sample by way of rotary joints held by holders mounted in a force introducing machine, such as a universal material testing machine. A testing device of this type is disclosed, for example, in the in-house publication of Roell+Korthaus, Amsler-Prüfmaschinen AG (Schaffhausen, Switzerland), entitled "Prüfsysteme" [Testing Systems], Specification 205, pages 8–9, under the heading "4-Punkt-Biegevorrichtung" [Four-Point Bending Device]. Testing devices of this type are employed for mechanical materials testing, particularly to test the service life and service reliability of semi-finished products and components, particularly printed circuit boards.

The prior art four-point testing device for alternating bending made by Roell+Korthaus is composed of four clamps for holding the sample. The clamps are held in a pivotal manner by spring elements. However, this way of clamping in the sample generates structurally caused, undesirable tensile and compressive forces in the sample in addition to the bending stresses. As a result, the stroke of this testing device is limited to ±0.6 mm according to the manufacturer's information.

An article by K. G. Kiessling, entitled "Untersuchungen zur Zuverlässigkeit von Lötverbindungen in der SMD-Technik" [Tests Regarding the Reliability of Solder Connections in SMD (Surface Mounted Device) Technology], in SMT/ASIC/Hybrid 1990 Congress, May 15–17, 1990, Nürnberg (published by Hüthig Buch Verlag, Heidelberg, 1990), pages 423–431, further describes a testing device for performing three-point fatigue strength tests under alternating bending stresses. Testing devices of this type have the drawback that they stress the samples to be examined with a bending moment that changes linearly over the length of the sample.

SUMMARY OF THE INVENTION

It is an object of the present invention to provide a testing device of the above-mentioned type with which a sample to be examined, particularly a printed circuit board that is equipped with components, can be bent in four-point fatigue tests under alternating bending stresses with the least possible tensile stresses being superposed on the bending stress and in which the zero passages are to be as free of play as possible.

The above and other objects are accomplished in accordance with the invention by the provision of a testing device for performing four-point fatigue strength tests of a sample by applying alternating bending stresses to the sample, comprising: four rotary joints, each rotary joint including a pair of individual, spaced-apart rollers so that a sample can be guided between the individual rollers of the respective pairs of rollers, each roller having a longitudinal axis and being rotatable about its own longitudinal axis; first and second plates adapted to be fixed in a force introducing machine so that the first and second plates are relatively movable toward and away from one another; four holders each for supporting a respective one of the rotary joints, two of the holders being mounted to the first plate, with a third and fourth ones of the holders being disposed between the two holders and being mounted to the second plate, and each holder including means for mounting its rotary joint so that the individual rollers of the rotary joint are rotatable about a common rotation axis.

The invention will now be described in greater detail with reference to two drawing figures.

BRIEF DESCRIPTION OF THE DRAWINGS

FIG. 1 is a front view, in partial section, of a preferred embodiment of the testing device according to the invention.

FIG. 2 is a side view of part of the preferred embodiment of the testing device according to the invention shown in FIG. 1.

DETAILED DESCRIPTION OF PREFERRED EMBODIMENTS

The testing device of FIG. 1 is composed of two similarly constructed components, one of which is stationary and the other of which is vertically movable relative to the stationary component within the coordinate system of the testing device, as indicated by a double arrow 12. The movable component is composed of two rotary joints 1 and 2 arranged between third and fourth rotary joints 3 and 4 of the stationary component. Rotary joints 1, 2, 3, and 4 are each equipped with holders 5, 6, 7, and 8, respectively, with the holders 7 and 8 of rotary joints 3 and 4, respectively, of the stationary component each being fastened to a base plate 10 of a force introducing machine (not shown), while holders 5 and 6 of rotary joints 1 and 2, respectively, are fastened to a plate 11 of a movable component of the force introducing machine. Base plate 10 is attached firmly (for example) to the bed of the machine. Plate 11 is clamped in the manner of a pull rod into an upper sample receptacle (not shown) of the machine and is movable vertically relative to base plate 10 as shown by double arrow 12. Generally, a force introducing machine such as, for example, a universal material testing machine, is suitable for use in connection with the invention. Holders 7 and 8 of the two rotatable, but vertically stationary rotary joints 3 and 4 are suitably mounted for horizontal displacement on base plate 10, that is, parallel to the surface of the base plate. Holders 5 and 6 of movable rotary joints 1 and 2 are correspondingly suitably mounted to be movable horizontally on plate 11 (indicated in each case in FIG. 1 by horizontally extending arrows).

The individual rotary joints 1, 2, 3, and 4 are each essentially composed of a pair of rollers of which, for example, roller pair 20, 21 of movable rotary joint 2 is shown in FIG. 1 and roller pair 40, 41 of the vertically stationary rotary joint 4 is shown in FIG. 2. Thus, the description herein of rotary joints 2 and 4 is equally applicable to rotary joints 1 and 3, respectively. The rollers of the individual roller pairs 20, 21 and 40, 41, respectively, are each mounted in the respectively associated rotary joint 2 and 4, so as to rotate about their longitudinal axis 201, 211 and 401, 411, respectively. Additionally, individual rotary joints 1, 2, 3, and 4 are rotatably mounted in their respectively associated holders 5, 6, 7, and 8 so that their rotation axes 13, 23, 33, and 43 lie centrally between the longitudinal axes 201, 211, etc. of the two respectively associated rollers 20, 21, etc. and parallel thereto.

At this point it should be emphasized again that reference to the two rotary joints 2 and 4 can be considered as exemplary only. In principle, the two movable rotary joints 1 and 2 and their mounts 5 and 6 coincide in structure and function and the two stationary rotary joints 3 and 4 and their holders 7 and 8 coincide with respect to structure and function.

The rollers of the individual roller pairs 20, 21 and 40, 41, respectively, have their longitudinal axes 201, 211 and 401, 411, respectively, aligned parallel to one another and, in the zero position (starting position) when sample 9 is unbent, they lie vertically above one another. The rotation axes 13, 23, 33, and 43 of rotary joints 1, 2, 3, and 4 each constitute a common rotation axis for the two rollers of the respective roller pairs.

As can be seen in FIG. 2, the common rotation axis 43 is defined by two collinearly arranged shaft stubs 43a, 43b, which project beyond side walls 42a, 42b of rotary joint 4 and are pivotally mounted in the corresponding side walls 8a, 8b of holder 8. Longitudinal axes 401, 411 of rollers 40, 41, respectively, are defined by axles or shafts 401a and 411a, respectively which are rotatably mounted in corresponding side walls 42a and 42b of rotary joint 4. Rollers 40 and 41 and their respective longitudinal axes 401 and 411 are rotatable about common rotation axis 43 due to the mechanical linkage of the longitudinal axes 401 and 411 with common rotation axis 43 formed by side walls 42a and 42b. Rotary joint 4 is thus rotatable within holder 8. The same is similarly true of the other rotary joints 1, 2 and 3 which rotate within their associated holders 5, 6 and 7, respectively.

The spacing between the rollers of each roller pair 20, 21 and 40, 41, etc., is infinitely variable for each roller pair independently of the other roller pairs. The shafts defining the longitudinal axes of the individual rollers of rotary joints 1, 2, 3 and 4 are each mounted in guides having the form of elongated grooves in the corresponding side walls of the associated rotary joints. Elongated grooves 45 and 46 in rotary joint 4 of FIG. 1 are representative of the guides for the individual rollers. The shafts of the individual rollers are fixed against horizontal and/or vertical escape from the respective guides.

The individual rollers 20, 21, etc., of rotary joints 1, 2, 3 and 4 are held within the pair and relative to the other roller pairs so that sample 9 to be examined can be inserted between the rollers of the individual roller pairs so that it is possible to clamp sample 9 in without play or tension, with the individual alignment lines of the common rotation axes 13, 23, 33, and 43, of the individual roller pairs extending centrally, or at least approximately centrally, within the sample to be tested.

The bearings of rollers 20, 21; 40, 41, etc., and/or the bearings of shaft stubs 43a, 43b, respectively, are preferably configured as roller or slide bearings, particularly as ball bearings or pin bearings.

The material of the rollers may be adapted to the material of the sample. It is also possible to surface treat the rollers such as, for example, to coat them (with plastic by CVD [chemical vapor deposition], or PVD [physical vapor deposition], etc.) or heat treat them pursuant to the requirements of the known rolling or surface pressing art, without having to modify the remaining components of the testing device.

In the starting position before the four-point fatigue strength test under alternating bending stresses is performed, the space between base plate 10 and movable plate 11 is selected to be such that the individual roller pairs all have the same or approximately the same distance from base plate 10. The distance between the individual rollers in the individual roller pairs is selected so that the sample 9 to be examined, for example a printed circuit board, can easily be introduced between the rollers of the individual roller pairs. Then the individual roller pairs are held within themselves and relative to one another and their positions are fixed so that sample 9 can be clamped in without play or bending stresses.

Thereafter, the four-point fatigue strength tests under alternating bending stresses are performed in that plate 11 is moved vertically up and down (within the coordinate system of the testing device) relative to the starting position (starting or zero point), thus bending sample 9 around its zero point alternatingly toward the top and bottom. Due to the fact that, on the one hand, individual rollers 20, 21, etc., of rotary joints 1, 2, 3 and 4 themselves are mounted so as to rotate about their longitudinal axes 201, 211, etc., and rotary joints 1, 2, 3 and 4 are mounted to each rotate about the common rotation axes 13, 23, 33, 43, respectively, the individual rotary joints 1, 2, 3, and 4 are able to easily adapt their position to the bending of sample 9 by rolling or turning their position so that an imaginary connecting surface between longitudinal axes of the individual rollers of each roller pair, for example between longitudinal axes 201 and 211, is always perpendicular to or almost perpendicular to the sample surface during the entire period when sample 9 is being tested for fatigue strength under alternating bending. Thus, it is possible to perform a fatigue test under alternating bending stresses practically without tensile stresses on sample 9 which nevertheless is held securely in a defined position during the experiment by rotary joints 1, 2, 3, and 4. In a preferred embodiment, the device according to the invention permits, for example, bending paths of up to about ±10 mm at bending forces between 0.1 N and 1000 N.

It is understood that, within the knowledge of the person skilled in the art, the invention can also be expanded and modified in order to meet, for example, requirements for a design that is specific for a manufacturing process and/or an intended use and/or user friendliness, or to be able to employ other samples of different shapes (e.g., tubes) or dimensions (e.g. railroad tracks) or of a different material (e.g., steel, ceramics) without this having to be described in greater detail here.

Thus it is also conceivable within the scope of the invention, for example, to exchange the positions of the movable component and the stationary component and/or to arrange the stationary rotary joints between the movable rotary joints.

It is further conceivable within the scope of the invention for base plate 10 of the two stationary rotary joints 3 and 4 not to be fastened to the material testing machine bed but to be clamped directly or by way of a pin, similarly to plate 11 of FIG. 1, into a lower sample receptacle in the material testing machine. Then it would be possible to make the stationary component movable as well so that, for example, both components of the testing device are able to perform mutually vertical (collinear) movements within the coordinate system of the testing device.

Although the testing device is designed so that the movable component performs a defined linear movement perpendicular to the stationary component within the coordinate system specific to the testing device, the testing device as such can be oriented in space in any desired orientation so that, for example, the movable component of the testing device also is able to perform a horizontally linear movement or an obliquely linear movement within the coordinate system specific to space or to the material testing machine.

Finally, if the individual rollers and rotary joints are held in their holders only on one side and/or the holders are constituted by pairs of movable, fixable arms, manufacture and operation can be even further simplified. In particular, plates 10 and 11 of FIG. 1 could be omitted as a result of these measures.

The essential advantages of the testing device according to the invention are primarily the following:

the structure of the testing device for testing alternating bending strength is simple and easily manufactured; and the imaginary connecting surface between the two longitudinal axes of the rollers of each roller pair is perpendicular to the sample surface during the entire period of testing the sample for fatigue strength under alternating bending stresses, thus minimizing annoying ancillary forces and making them calculatable so that they can be neglected or considered in a simple manner in the course of the evaluation of the tests.

Thus, the present invention has created an economical testing device in which the bending moment is constant over a greater length of the sample, systematic measuring errors are excluded. In particular, additional tensile stresses, particularly in the longitudinal direction, are eliminated or at least minimized particularly for less intensive bending of the sample.

Further advantages of the invention are the following:

a zero passage without play is ensured;

the contact pressure of the rollers against the sample can be infinitely varied for each roller pair independently of the other roller pairs;

it is possible to finely match the material of roller and sample without having to modify other components of the device; and it is possible to vary the size of the sample by adjusting the existing testing device or by proportionally enlarging/reducing the size of the device.

Obviously, numerous and additional modifications and variations of the present invention are possible in light of the above teachings. It is therefore to be understood that within the scope of the appended claims, the invention may be practiced otherwise than as specifically claimed.

What is claimed is:

1. A testing device for performing four-point fatigue strength tests of a sample by applying alternating bending stresses to the sample, comprising:

four rotary joints, each rotary joint including a pair of individual, spaced-apart rollers so that a sample can be guided between the individual rollers of the respective pairs of rollers, each roller having a longitudinal axis and being rotatable about its own longitudinal axis;

first and second plates adapted to be fixed in a force introducing machine so that said first and second plates are relatively movable toward and away from one another; and four rotary joint holders each for supporting a respective one of the rotary joints, two of the rotary joint holders being mounted to said first plate, with third and fourth ones of the rotary joint holders being disposed between said two rotary joint holders and being mounted to said second plate, and each rotary joint holder including means for mounting its rotary joint so that the individual rollers of the rotary joint are rotatable about a common rotation axis.

2. A testing device as defined in claim 1, wherein the rollers of said rotary joints and their longitudinal axes are aligned parallel to one another and, in a starting position of said testing device, the individual rollers of each rotary joint are arranged approximately one behind the other in the direction of relative movement of said first and second plates and their associated rotary joints.

3. A testing device as defined in claim 1, wherein the common rotation axis of each rotary joint extends centrally and parallel to the longitudinal axes of the two rollers of the respectively associated roller pair.

4. A testing device as defined in claim 1, wherein each rotary joint includes infinitely variable mounting means for mounting the individual rollers so that the distance between the two rollers of each roller pair is infinitely variable.

5. A testing device as defined in claim 4, wherein the individual rollers include shaft means for defining the longitudinal axes of the individual rollers and said rotary joints each include mounting means defining guides for mounting the individual rollers so that the shaft means of each individual roller rotates in respectively associated ones of said guides, each guide including means for fixing said shaft means against horizontal and/or vertical escape.

6. A testing device as defined in claim 5, wherein said rotary joints each include opposing side walls and said guides each comprise an elongated groove in the corresponding side wall of the associated rotary joint.

7. A testing device as defined in claim 6, wherein said rotary joints each include two mutually collinear shaft stubs projecting outwardly of a respective one of said opposing side walls to define a respective one of said common rotation axes and being mechanically connected with the shaft means of the individual rollers of the associated rotary joint by said opposing side walls.

8. A testing device as defined claim 7, wherein each said rotary joint holder includes means for mounting the shaft stubs of a respective one of said rotary joints, and said means for mounting the shaft stubs and said means for mounting the individual rollers comprise one of roller and slide bearings.

9. A testing device as defined in claim 4, further comprising means for adjusting said roller joints relative to one another so that, together with said infinitely variable mounting means of the individual rollers or each roller joint, the sample can be clamped in said testing device without play or bending stresses and with the common rotation axes of the individual roller pairs extending at least approximately centrally within the sample to be tested.

10. A testing device as defined in claim 1, wherein one of said first and second plates is adapted for being attached to a stationary component of the force introducing machine and the other of said first and second plates is adapted for being fixed to a component of the force introducing machine which is movable so that the rotary joints of said other plate can be moved toward and away from the rotary joints of said one plate.

11. A testing device as defined in claim 10, further comprising means for mounting each of said rotary joint holders to a respective one of said plates for displacement in a direction parallel to the associated plate.

12. A testing device as defined in claim 1, wherein said rotary joints each comprise a roller holder and means for mounting the individual rollers of a roller pair in a respective one of said roller holders so that the individual rollers are held only on one side.

13. A testing device as defined in claim 1, further comprising means for mounting the rotary joints to a respective one of the rotary joint holders so that each rotary joint is held in its respective rotary joint holder only on one side.

14. A testing device as defined in claim 1, wherein said rotary joint holders comprise pairs of movable, fixable arms.

15. A testing device as defined in claim 1, further comprising auxiliary means for varying the distance between the two rollers of each roller pair so that the common rotation axis of each roller pair always extends centrally between the two associated roller longitudinal axes.

* * * * *